US00PP20397P2

(12) United States Plant Patent
Kobayashi

(10) Patent No.: US PP20,397 P2
(45) Date of Patent: Oct. 6, 2009

(54) POINSETTIA PLANT NAMED 'PER11406'

(50) Latin Name: *Euphorbia pulcherrima*
Varietal Denomination: PERR11406

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 12/152,682

(22) Filed: May 14, 2008

(51) Int. Cl.
*A01H 5/00* (2006.01)

(52) U.S. Cl. ..... Plt./303

(58) Field of Classification Search ..... Plt./303
See application file for complete search history.

*Primary Examiner*—Susan B McCormick Ewoldt
(74) *Attorney, Agent, or Firm*—C. A. Whealy

(57) ABSTRACT

A new and distinct cultivar of Poinsettia plant named 'PER11406', characterized by its uniform, upright, outwardly spreading and mounded plant habit; vigorous growth habit; freely branching habit; dark green-colored leaves; early season flowering response; inflorescences with pink and creamy white bi-colored flower bracts; and excellent post-production longevity.

1 Drawing Sheet

Botanical designation: *Euphorbia pucherrima.*
Cultivar denomination: 'PER11406'.

CLOSELY RELATED APPLICATIONS

Title: Poinsettia Plant Named 'PER11306'

Applicant: Ruth Kobayashi

Filed: Concurrently with this application (U.S. Plant patent application Ser. No. 12/152,681)

BACKGROUND OF THE INVENTION

The present invention relates to a new and distinct cultivar of Poinsettia plant, botanically known as *Euphorbia pulcherrima* Willd., and hereinafter referred to by the name 'PER11406'.

The new Poinsettia is a naturally-occurring whole plant mutation of *Euphorbia pulcherrima* Willd. '30-05', not patented. The new Poinsettia was discovered and selected by the Inventor as a single plant within a population of plants '30-05' in a controlled greenhouse environment in Encinitas, Calif. on Dec. 19, 2005.

Asexual reproduction of the new Poinsettia by terminal vegetative cuttings in a controlled greenhouse environment in Encinitas, Calif. since February, 2006, has shown that the unique features of this new Poinsettia are stable and reproduced true to type in successive generations of asexual reproduction.

SUMMARY OF THE INVENTION

The new Poinsettia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER11406'. These characteristics in combination distinguish 'PER11406' as a new and distinct cultivar of Poinsettia:

1. Uniform, upright, outwardly spreading and mounded plant habit.
2. Vigorous growth habit.
3. Freely branching habit.
4. Dark green-colored leaves.
5. Early season flowering response; under natural season conditions, plants flower in about eight weeks in Encinitas, Calif.
6. Inflorescences with pink and creamy white bi-colored flower bracts.
7. Excellent post-production longevity.

In side-by-side comparisons conducted in Encinitas, Calif., plants of the new Poinsettia differed from plants of the parent, '30-05', primarily in flower bract color as plants of '30-05' have pink-colored flower bracts. In addition, plants of the new Poinsettia have darker green-colored leaves than '30-05'.

Plants of the new Poinsettia can be compared to plants of the *Euphorbia pulcherrima* Willd. 'PER11306', U.S. Plant patent application filed concurrently. Plants of the new Poinsettia and 'PER11306' differ primarily in flower bract color as plants of 'PER11306' have yellowish white-colored flower bracts.

Plants of the new Poinsettia can be compared to plants of the *Euphorbia pulcherrima* Willd. 'PER10603', disclosed in U.S. Plant Pat. No. 18,199. In side-by-side comparisons conducted in Encinitas, Calif., plants of the new Poinsettia differed from plants of 'PER10603' in the following characteristics:

1. Plants of the new Poinsettia were more vigorous than plants of 'PER10603'.
2. Plants of the new Poinsettia flowered about four days earlier than plants of 'PER10603' under natural season conditions.

BRIEF DESCRIPTION OF THE PHOTOGRAPHS

The accompanying photographs illustrate the overall appearance of the new Poinsettia. These photographs show the colors as true as it is reasonably possible to obtain in colored reproductions of this type. Colors in the photographs may differ slightly from the color values cited in the detailed botanical description which accurately describe the colors of the new Poinsettia.

The photograph at the bottom of sheet comprises a side perspective view of a typical flowering plant of 'PER11406' grown in a container.

The photograph at the top of the sheet is a close-up view of typical inflorescences of 'PER11406'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and the following observations and measurements describe plants grown in Encinitas, Calif. during the winter in a polyethylene-covered greenhouse and under conditions and practices which approximate those generally used in commercial Poinsettia production. During the production of the plants, day temperatures averaged 24° C., night averaged 19° C. and light levels were about 4,000 foot-candles. Measurements and numerical values represent averages for typical flowering plants. Single plants were grown in 15.25-cm pots and pinched one time. Plants were 14 weeks old when the photographs and the detailed description were taken.

Botanical classification: *Euphorbia pulcherrima* 'PER11406'.

Parentage: Naturally-occurring whole plant mutation of the *Euphorbia pulcherrima* Willd. '30-05', not patented.

Propagation:

*Type.*—Terminal vegetative cuttings.

*Time to initiate roots.*—About five to seven days at 21° C.

*Time to produce a rooted young plant.*—About four weeks at 21° C.

*Root description.*—Fibrous; white in color.

Plant description:

*Plant habit and form.*—Uniform, upright, outwardly spreading and mounded plant habit; inverted triangle. Inflorescences positioned above the foliar plane. Vigorous growth habit.

*Plant height.*—About 30 cm.

*Plant diameter or spread.*—About 48 cm.

*Lateral branch description.*—Quantity: Freely branching habit, about nine lateral branches develop after pinching. Length: About 25 cm to 27 cm. Diameter: About 5 mm. Internode length: About 2 cm. Strength: Strong. Texture: Smooth, glabrous. Color: Close to 146B.

*Foliage description.*—Arrangement: Alternate, simple. Length: About 13.3 cm. Width: About 11.2 cm. Shape: Ovate with occasional shallow lobes. Apex: Acuminate. Base: Obtuse. Margin: Entire; occasional shallow lobes. Venation pattern: Pinnate. Texture, upper surface: Smooth, glabrous. Texture, lower surface: Pubescence along venation. Surface: Rugose. Color: Developing foliage, upper surface: Close to 146A. Developing foliage, lower surface: Close to 146B. Fully developed, upper surface: Close to 147A; venation, close to 146C. Fully expanded foliage, lower surface: Slightly more grey than 147B; venation, close to 147C. Petiole: Length: About 5 cm. Diameter: About 3 mm. Texture, upper and lower surfaces: Smooth, glabrous. Color, upper and lower surfaces: Close to 146C.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Early season flowering; response time, plants flower about eight weeks under natural season conditions in Encinitas, Calif.

*Post-production longevity.*—Excellent post-production longevity; plants of the new Poinsettia maintain good substance and bract color for about four weeks under interior conditions.

*Inflorescence size.*—Diameter: About 35 cm. Height (depth): About 7.5 cm.

*Flower bracts.*—Quantity per inflorescence: About 20. Length, largest bracts: About 14 cm. Width, largest bracts: About 9.8 cm. Shape: Elliptical; occasionally with shallow lobes. Apex: Acuminate. Base: Cuneate to obtuse. Margin: Entire; occasionally with shallow lobes. Texture, upper and lower surfaces: Smooth, glabrous. Aspect: About 30° from horizontal to nearly horizontal with development. Venation pattern: Pinnate. Color: Developing or transitional bracts, upper surface: Close to 4C; central irregular patches of 48B. Developing or transitional bracts, lower surface: Close to 4C; central irregular patches of 49A. Fully expanded bracts, upper surface: Close to 10C; central irregular patches of 50C; venation, similar to lamina. Color becoming closer to 2D with central irregular patches of 50C with development. Fully expanded bracts, lower surface: Close to 10D; central irregular patches of 51C; venation, similar to lamina. Bract petiole: Length: About 1.6 cm. Diameter: About 1.5 mm. Texture, upper and lower surfaces: Smooth, glabrous. Color, upper and lower surfaces: Close to 160B.

*Cyathia.*—Quantity per corymb: About ten to twelve. Diameter of cyathia cluster: About 2.8 cm by 3.2 cm. Length: About 1.1 cm. Width: About 6 mm. Shape: Ovoid. Color, immature: Close to 146A. Color, mature: Close to 146C. Nectaries: Quantity per cyathium: About one or two. Size: About 2 mm by 3 mm. Color: Close to 15A.

*Peduncles.*—Length: About 4 mm. Diameter: About 2 mm. Strength: Strong. Aspect: Mostly upright to outwardly. Texture: Smooth, glabrous. Color: Close to 146D.

*Reproductive organs.*—Stamens: Quantity per cyathium: About 15. Anther shape: Oval; bi-lobed. Anther length: About 1 mm. Anther color: Close to 160A. Amount of pollen: Scarce. Pollen color: Close to 6A. Pistils: Plants of the new Poinsettia do not develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 30° C.

It is claimed:

1. A new and distinct Poinsettia plant named 'PER11406' as illustrated and described.

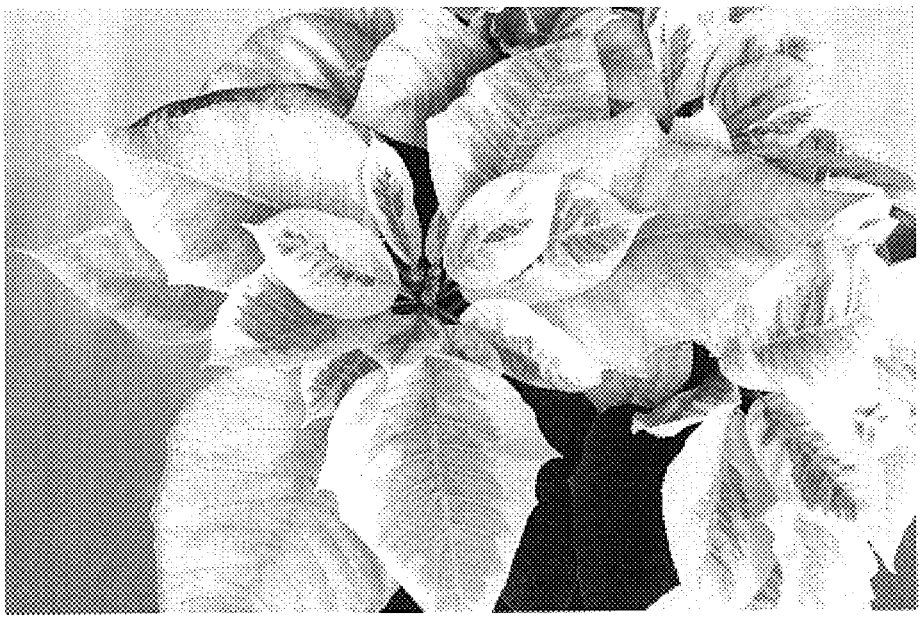
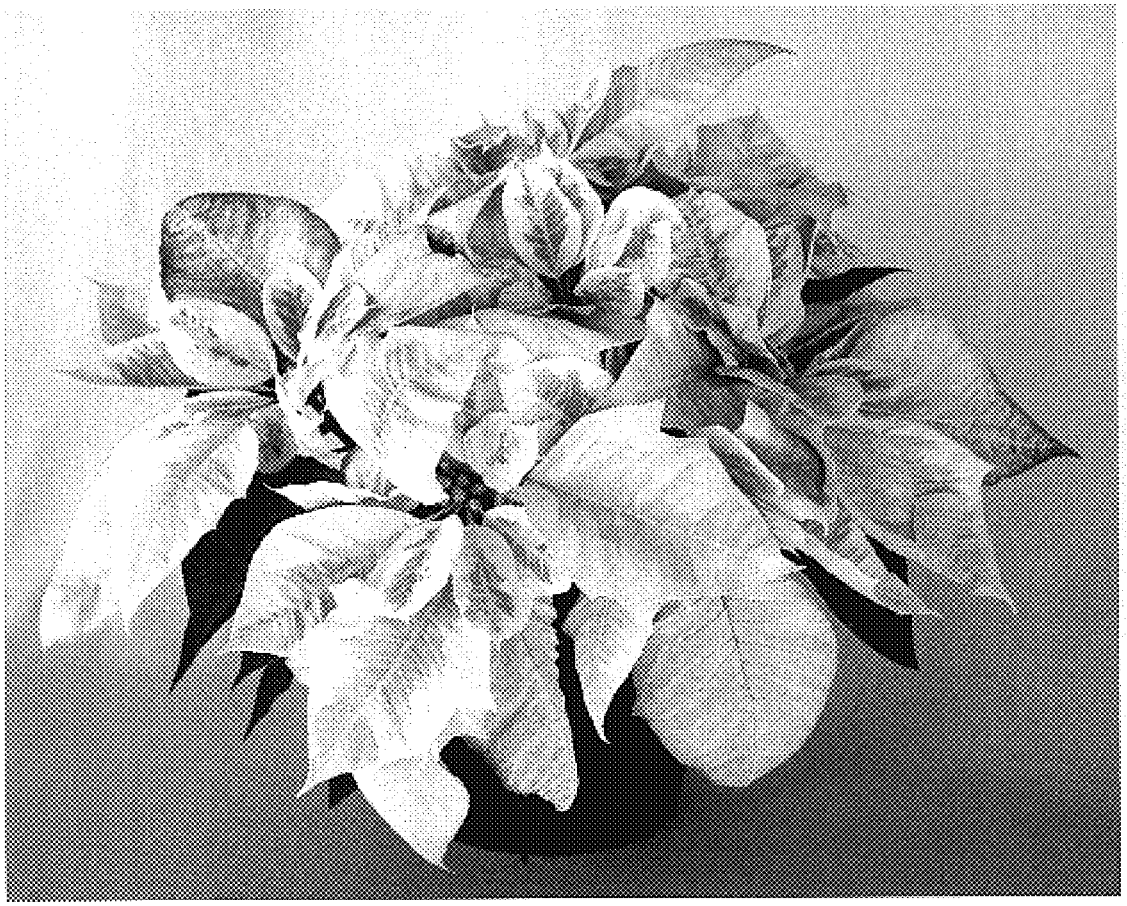

* * * * *